United States Patent [19]

Guglielmi et al.

[11] Patent Number: 5,569,245
[45] Date of Patent: Oct. 29, 1996

[54] DETACHABLE ENDOVASCULAR OCCLUSION DEVICE ACTIVATED BY ALTERNATING ELECTRIC CURRENT

[75] Inventors: Guido Guglielmi, Santa Monica; Cheng Ji, Los Angeles, both of Calif.

[73] Assignee: The Regents of the University of California, Oakland, Calif.

[21] Appl. No.: 323,662

[22] Filed: Oct. 17, 1994

Related U.S. Application Data

[63] Continuation-in-part of Ser. No. 311,508, Sep. 23, 1994, which is a continuation of Ser. No. 840,211, Feb. 24, 1992, Pat. No. 5,354,295, which is a continuation-in-part of Ser. No. 492,717, Mar. 13, 1990, Pat. No. 5,122,136.

[51] Int. Cl.$^6$ .................................................. A61B 17/39
[52] U.S. Cl. .................. 606/49; 606/32; 606/40
[58] Field of Search ................................. 606/32, 41, 49, 606/40

[56] References Cited

U.S. PATENT DOCUMENTS 5,122,136  6/1992  Guglielmi et al. ...................... 606/41
5,354,295  10/1994 Guglielmi et al. ...................... 606/32

*Primary Examiner*—Lee S. Cohen
*Attorney, Agent, or Firm*—Daniel L. Dawes

[57] ABSTRACT

An apparatus is provided for electrocoagulating blood and tissue at an occlusion site by means of application of an alternating signal or current through a detachable coil on the end of a microcatheter. A Guglielmi Detachable Coil (GDC) is preferably used in the combination with radio frequency energy to cause local heating at the coil. Once carbonization of blood at the detachment zone of the GDC coil occurs, the impedance of the entire system increases. The impedance increase is detected to automatically turn off the alternating current and then to apply a direct current to electrolytically detach the GDC coil from the microcatheter.

21 Claims, 1 Drawing Sheet

DETACHABLE ENDOVASCULAR OCCLUSION DEVICE ACTIVATED BY ALTERNATING ELECTRIC CURRENT

BACKGROUND OF THE INVENTION

This application is a continuation-in-part of U.S. Pat. application Ser. No. 08/311,508, filed Sep. 23, 1994, which is a continuation of U.S. Pat. application Ser. No. 07/840,211, filed Feb. 24, 1992, now U.S. Pat. No. 5,354,295, which is a continuation-in-part of U.S. Pat. application Ser. No. 07/492,717, filed Mar. 13, 1990, now U.S. Pat. No. 5,122,136.

1. Field of the Invention

The invention relates to the field of electrocoagulation, and in particular to the use of alternating currents to form endovascular occlusions.

2. Description of the Prior Art

Occlusion of vascular structures by endovascular catheters is currently realized though the use of detachable balloons, injectable glue, detachable or pushable coils, and injectable particles. Detachable balloons are of such a nature that they can only be practically used in large vessels. The use of injectable glue is limited by the difficulty of controllable delivery to the desired occlusion site. Detachable and pushable coils are effective, but in some cases are not sufficiently thrombogenic. The use of injectable particles suffers from their relative invisibility in fluoroscopy and the difficulty in controlling their ultimate disposition at the desired occlusion site. In many prior art technologies the coagulation wire must be ripped out of the clot, usually causing considerable disruption or even reopening the occlusion.

The use of both alternating and direct current for creating electrocoagulation is well known. See. Gold et al., "Transarterial Electrocoagulation Therapy of a Pseudoaneurysm in the Head Of the Pancreas," American Journal of Roentgenology, Volume 125, No. 2, at 422 (1975); Thompson et al., "Vessel Occlusion with Transcatheter Electrocoagulation: Initial Clinical Experience," Diagnostic Radiology at 335 (November 1979); Thompson et al., "Transcatheter Electrocoagulation: A Therapeutic Angiographic Technique for Vessel Occlusion," Investigative Radiology at 146 (March–April 1977); Phillips, "Transcatheter Electrocoagulation of Blood Vessels," Investigative Radiology at 295 (September–October 1973); and Phillips et al., "Experimental Closure of Ateriovenous Fistula by Transcatheter Electrocoagulation," Diagnostic Radiology 115:319 (May 1975). However, each of these experimental investigations were generally performed in larger vessels and did not establish controllability, nor efficacy for use in smaller vessels.

Therefore, what is needed is a clinical occlusive device which is visible, biocompatible, controllable in that it can be detached at will at a desired site even distal to the delivery microcatheter, which is directable, efficacious in coagulating blood and vessel and usable in small vessels without the risk of causing disruption or reopening the occlusion at the end of the treatment.

BRIEF SUMMARY OF THE INVENTION

The invention is an apparatus for selectively providing endovascular occlusion in a patient comprising a delivery wire guidable to or near an endovascular occlusion site. A detachable coil is temporarily and selectively coupled to the delivery wire. An alternating current generator selectively is coupled to the detachable coil to provide current to the coil to effect electrocoagulation. As a result, a controllable occlusive apparatus efficacious and usable in small vessels is provided.

The apparatus further comprises a direct current generator selectively coupled to the detachable coil. A switch selectively couples either the alternating current generator and direct current generator to the detachable coil or both. In the preferred embodiment the coil is a GDC coil. The alternating and direct current generators are variably controllable and the controllable alternating current generator is frequency controllable.

The apparatus further comprises a sensing circuit for determining when a predetermined state of electrocoagulation is achieved at or near the detachable coil. The sensing circuit senses impedance of the detachable coil within the patient. The apparatus further comprises a control circuit for selectively initiating detachment of the coil when the sensing circuit determines the predetermined state of electrocoagulation has been achieved.

The alternating current generator serves to ohmically heat the detachable coil and surrounding blood tissues and/or dielectricly heat the detachable coil and surrounding blood tissues at a radio frequency.

The invention is also defined as an apparatus for creating an endovascular occlusion at a selectively occlusion site comprising a conductive delivery wire and a selectively disposable and detachable conductive coil coupled to the delivery wire and disposable by the delivery wire at or near the occlusion site. An alternating current signal source is electrically coupled to the delivery wire and coil for providing a source of heating energy at the coil. As a result, the apparatus is a controllable occlusive device usable and efficacious in small vessels.

The detachable coil is electrolytically detachable or mechanically detachable. The apparatus further comprises a control circuit for determining when a predetermined degree of electrocoagulation has occurred at the coil and then for detaching the coil from the delivery wire. A direct current signal source is electrically coupled to the detachable coil and the control circuit turns the alternating current signal source off when the predetermined degree of electrocoagulation has occurred and turns the direct current signal source on to detach the coil from the delivery wire.

The invention is also characterized as a method of forming a vascular occlusion comprising providing a conductive delivery wire and disposing a conductive coil coupled to the delivery wire at or near a selected occlusion site. An alternating current is applied to the coil to coagulate the occlusion site. A determination is made whether a predetermined amount of electrocoagulation has occurred at the occlusion site. The alternating current through the coil is terminated when the step of determining establishes that the predetermined electrocoagulation has occurred. The coil is then detached from the delivery wire to leave the coil at the occlusion site. As a result, an occlusion is efficaciously provided in a small vessel.

In the preferred embodiment, detaching the coil from the delivery wire is performed automatically and the coil is electrolytically separated from the delivery wire.

The invention may be better visualized by now turning to the following drawings wherein like elements are referenced by like numerals.

The invention and its various embodiments may now be better understood by turning to the following detailed description.

DETAILED DESCRIPTION OF THE PREFERRED EMBODIMENTS

An apparatus is provided for electrocoagulating blood and tissue at an occlusion site by means of application of an alternating signal or current through a detachable conductive coil on the end of a delivery wire. A Guglielmi Detachable Coil (GDC) is preferably used in the combination with radio frequency energy to cause local heating at the coil. Once carbonization of blood at the detachment zone of the GDC coil occurs, the impedance of the entire system increases. The impedance increase is detected to automatically turn off the alternating current and then to apply a direct current to electrolytically detach the GDC coil from the delivery wire.

The apparatus of the invention uses a detachable microcatheter coil system and a source of alternating and direct electric current. The electrolytically detachable coil system is commercialized by Target Therapeutics of California as the Guglielmi Detachable Coil System (hereinafter defined as the GDC coil or system) and includes a source of direct current coupled to a microcatheter-guided wire with a mechanically or electrolytically detachable distal coil. Any one of the embodiments described in U.S. Pat. Nos. 5,122, 136; 5,226,911; and/or 5,354,295 may be used in the present apparatus. All of the U.S. Pat. Nos. 5,122,136; 5,226,911; and 5,354,295 are incorporated herein by reference as if set forth in their entirety. Mechanical means for detachment of the coil from the catheter is disclosed in U.S. Pat. Nos. 5,234,437 and 5,261,916 also incorporated herein by reference. The microcatheter detachable coil of the invention described above will therefore be variously referenced below as the "GDC coil" or by its generically equivalent description as a "non-thermally detachable coil."

Figure 1:
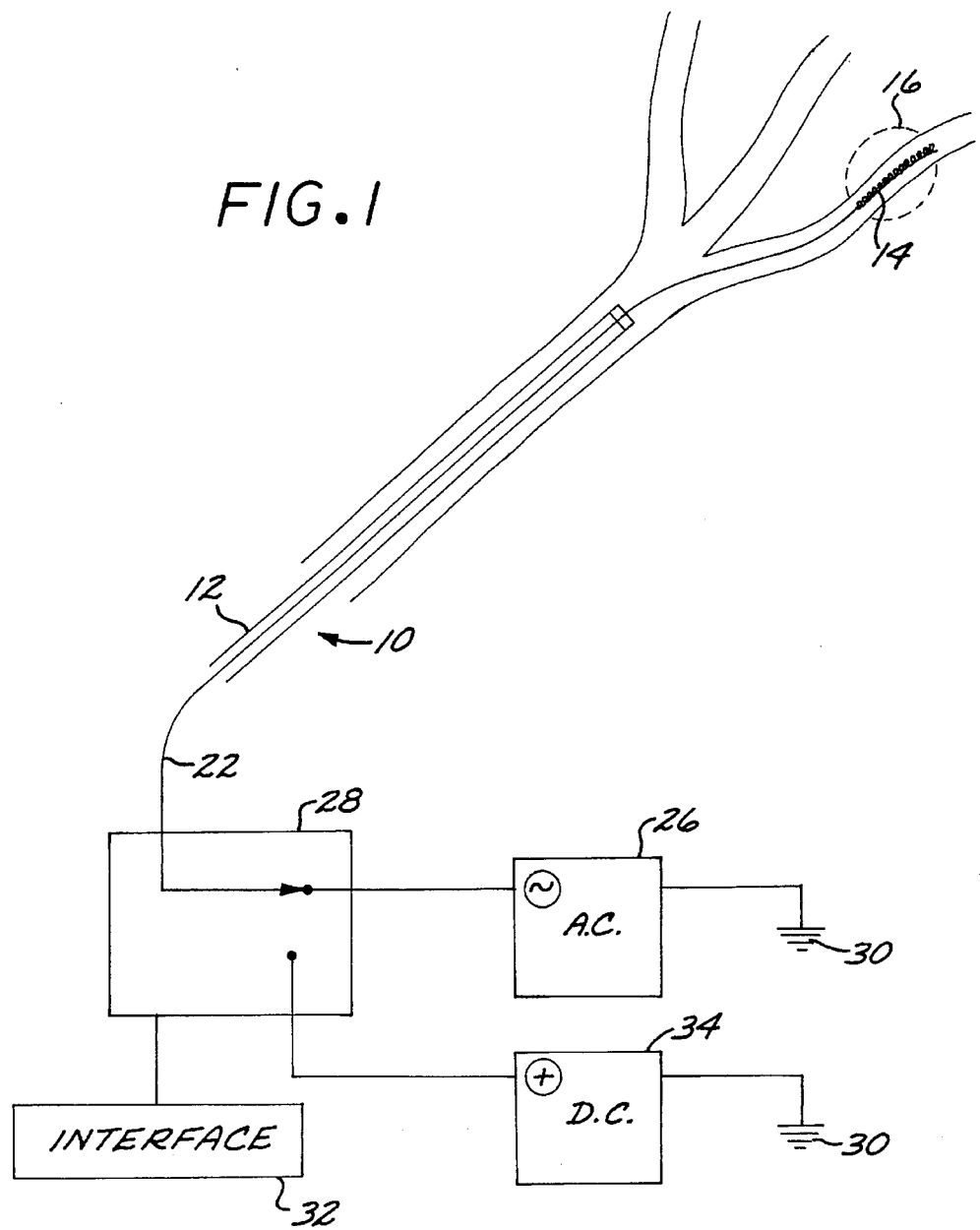
FIG. 1 is an idealized diagram of the apparatus of the invention.

FIG. 1 is a highly diagrammatic depiction of the apparatus as applied to form an endovascular occlusion. The GDC system, generally denoted by reference numeral 10, includes a guidable microcatheter 12, which in the illustrated embodiment is a tracker endovascular catheter as manufactured by Target Therapeutics, Inc. of Fremont, Calif. A GDC coil 14 is positioned at or proximate to a selected occlusion site 16, which is typically in a small vessel. GDC coil 14 is generally fabricated from platinum and may assume any physical shape, form or composition described in the foregoing incorporated patent references or known in the art. For example, GDC coil 14 may be straight, curved, circular, spiral, biased to form a preferred shaped, or completely limp and pliable, and may incorporate fibers or other equivalent micro-obstructive structures. The apparatus of FIG. 1 is particularly useful for arterial feeder occlusion of arteriovenous malformations, arteriovenous fistulae and vascular tumors.

Figure 2:
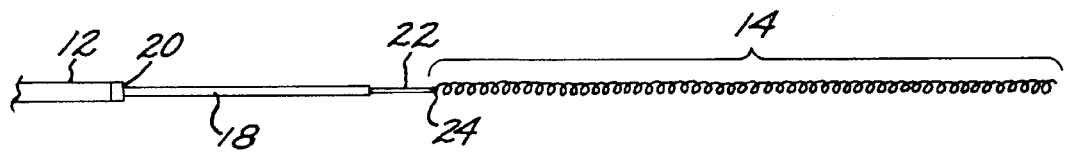
FIG. 2 is an enlarged view of one embodiment of the catheter for use in connection with the apparatus of FIG. 1.

For example, in the embodiment of FIG. 2, microcatheter 12 is shown as carrying an insulated guidewire 18 extending from catheter tip 20. At a predetermined position, insulated guidewire 18 is stripped of its insulation to provide a bare wire 22 connected at junction 24 to GDC coil 14.

GDC coil 14 is positioned at or near site 16 and an alternating signal generator 26 is connected through switching circuit 28 to a proximal end of delivery wire 22. As is conventional in the art, the alternating current is applied at a frequency, voltage, current repetition time, wave shape and other signal characteristic as may be desired to induce electrocoagulation of blood and body tissue in contact with and in the immediate vicinity of the uninsulated exposed portion of GDC coil 14 and wire 22 at the distal end of microcatheter 12. No electrocoagulation occurs in contact with or in the immediate vicinity of the insulated portion 18 of delivery wire 22.

A ground electrode 30 is provided to the patient through means of a conductive dermal adhesive pad, symbolically shown in FIG. 1 schematically as an electrical ground 30. The alternating signal or current applied through GDC coil 14 induces heating in the proximity of the noninsulated platinum portion of the GDC coil and/or the tissue such as the arterial or vessel wall and blood surrounding GDC coil 14. The insulated portion of the delivery wire should extend to almost 0.5 mm of the solder joint 24 holding coil 14, so that when alternating current or RF is applied, a clot will form substantially only around the detachable coil 14 and not the delivery wire. The frequency which is contemplated as being used and the present apparatus includes very low frequencies just above direct current to radio frequencies spanning the spectrum from less than 1 Hertz to many Gigahertz. For example, a frequency can be chosen to match a radio frequency absorption peak for any of the constituents at occlusion site 16, such as water. The proteins of the vascular structure or the blood are denatured by the heat and the shrinkage of the vascular wall and/or clotting of blood will occur. For example, it is well known that collagen fibers in the vascular wall are shrinkable at temperatures above 60 degrees centigrade.

The power provided by alternating signal generator 26 is variable by the operator through an interface unit 32 coupled thereto either directly or through switching circuit 28. Variability of the power, the voltage, current and repetition rate through interface 32 of the output of alternating current generator 26 is used to achieve vascular occlusion without damaging the vessel wall, and to minimize or even substantially avoid unintended or unwanted heating of the surrounding tissues. Alternating signal generator 26 is a variable alternating current generator with a voltage now only in the range of 0 to 70 volts and is preferably battery operated with rechargeable batteries. The waveform shape is selectable through interface 32 and typically may be sine wave, square wave, triangular wave or customized shapes with a variable frequency pulse rate.

The waveform of the alternating current signal is continuously monitored through interface 32 and vessel occlusion is instantly detected by changes in the shape of the waveform due to carbonization of the blood on the detachment zone in the proximity of junction 24 on GDC coil 14. This waveform change due to blood carbonization is determined by a change in the impedance of the system shown in FIG. 1. Therefore, interface 32 is contemplated as included an impedance detector which will automatically sound an audible signal to the operator or trigger an automatic turn off of the alternating current generator 26. Once sufficient coagulation has been determined to have occurred, GDC coil 14 is detached as described in the incorporated patent references by means of a direct current generated by direct current generator 34 and coupled through switching circuit 28 to delivery wire 22. Switching circuit 28 may be manually activated by the operator, or automatically programmed to switch over to deliver the proper direct current separating current at the completion of alternating current electrocoagulation.

GDC coils 14 are particularly effective in the apparatus of FIG. 1. In contrast to other types of endovascular coils, GDC coils 14 are detachable in place and distal from delivery catheter 12 after vessel occlusion has been achieved. Coils of various sizes, ranging from 0.005 to 0.2 inch in diameter, various shapes and configurations and softness utilizing platinum wire diameters in the range of 0.001 to 0.004 or more inch can be used as desired for coil 14. Platinum wires with different electrical resistances may be utilized.

Although the embodiment of FIG. 1 has been shown with alternating current generator 26 and direct current generator 34 as separate units, it is expressly contemplated that both units, as well as interface 32 together with an impedance detection circuit as described above, will be integrally incorporated within a single circuit. The impedance detector subcircuit thus automatically will turn off the alternating current signal and activate the direct current signal to detach the GDC coil 14. In this embodiment, the operator, after setting the initial parameters, need only then to turn on a single activate switch to cycle through a complete procedure. Acoustic or audio visual feedback can be provided to display both alternating current vessel occlusion and detachment of GDC coil 14. For example, both the direct current and alternating current components of the signal may be digitally generated through a personal computer software controlled interface. Power levels are low, being typically in the range of 0.1 to 20 watts so that the use of broadband generators is feasible. Alternatively, interface 32 may be used to selectively couple two or more separate generators to catheter 12 to completely cover the desire frequency bands discussed above.

While a conventional guidewire 22 is adequate for transmission of direct current to MHz signals, it is conceivable that power losses at higher frequencies in the GHz bands may become unacceptable. Therefore, guidewire 22 in these cases may be alternatively fabricated in the form of a flexible micro-coaxial cable, microwave transmission stripline or other transmission means now known or later devised as may be appropriate for carrying the power levels and frequencies disclosed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for selectively providing endovascular occlusion in a patient comprising:

a delivery wire guidable to or near an endovascular occlusion site;

a detachable conductive coil temporarily and selectively coupled to said delivery wire; and an alternating current generator selectively coupled to said detachable conductive coil, whereby a controllable occlusive apparatus efficacious and usable in small vessels is provided.

2. The apparatus of claim 1 further comprising:

a direct current generator selectively coupled to said detachable coil; and a switch means for selectively coupling said alternating current generator and direct current generator to said detachable coil.

3. The apparatus of claim 1 wherein said coil is a nonthermally detachable coil.

4. The apparatus of claim 1 wherein said alternating current generator is variably controllable.

5. The apparatus of claim 2 wherein said direct current generator is variably controllable.

6. The apparatus of claim 2 wherein said alternating and direct current generators are variably controllable.

7. The apparatus of claim 4 wherein said controllable alternating current generator is frequency controllable.

8. The apparatus of claim 1 further comprising a sensing circuit means for determining when a predetermined state of electrocoagulation is achieved at or near said detachable coil.

9. The apparatus of claim 8 wherein said sensing circuit means senses impedance of said detachable coil within said patient.

10. The apparatus of claim 8 further comprising a control circuit means for selectively initiating detachment of said coil when said sensing circuit means determines said predetermined state of electrocoagulation has been achieved.

11. The apparatus of claim 1 wherein said alternating current generator comprises means to ohmically heat said detachable coil and surrounding blood tissues.

12. The apparatus of claim 1 wherein said alternating current generator comprises means to dielectricly heat said detachable coil and surrounding blood tissues at a radio frequency.

13. An apparatus for creating an endovascular occlusion at a selectively occlusion site comprising:

a conductive delivery wire;

a selectively disposable and detachable conductive coil coupled to said delivery wire and disposable by said delivery wire at or near said occlusion site; and an alternating current signal source electrically coupled to said delivery wire and coil for providing a source of heating energy at said coil, whereby said apparatus is a controllable occlusive device usable and efficacious in small vessels.

14. The apparatus of claim 13 wherein said detachable coil is a nonthermally detachable coil.

15. The apparatus of claim 13 wherein said detachable coil comprises means for electrolytic detachment.

16. The apparatus of claim 13 wherein said detachable coil comprises means for mechanical detachment.

17. The apparatus of claim 13 wherein said alternating current signal source is a radio frequency signal source.

18. The apparatus of claim 13 further comprising a control circuit means for determining when a predetermined degree of electrocoagulation has occurred at said coil and then for detaching said coil from said delivery wire.

19. The apparatus of claim 18 further comprising a direct current signal source electrically coupled to said detachable coil and wherein said control circuit means turns said alternating current signal source off when said predetermined degree of electrocoagulation has occurred and turns said direct current signal source on to detach said coil from said delivery wire.

20. A method of forming a vascular occlusion comprising:

providing a conductive delivery wire;

disposing a conductive coil coupled to said delivery wire at or near a selected occlusion site;

applying an alternating current to said coil to coagulate said occlusion site;

determining whether a predetermined amount of electrocoagulation has occurred at said occlusion site;

terminating said alternating current through said coil when said step of determining establishes that said predetermined electrocoagulation has occurred; and detaching said coil from said delivery wire to leave said coil at said occlusion site, whereby an occlusion is efficaciously provided in a small vessel.

21. The method of claim 20 where detaching said coil from said delivery wire comprises automatically electrolytically separating said coil from said delivery wire.

* * * * *